United States Patent
Hardin-Naser

Patent Number: 6,159,167
Date of Patent: Dec. 12, 2000

[54] DISPOSABLE WOUND MEASURING DEVICE AND METHOD

[76] Inventor: Juel E. Hardin-Naser, 115 Village Dr. West, New Albany, Ind. 47150

[21] Appl. No.: 09/290,133

[22] Filed: Apr. 12, 1999

[51] Int. Cl.⁷ .................................................. A61B 5/00
[52] U.S. Cl. ........................................ 600/587; 33/512
[58] Field of Search .............................. 600/587; 604/117; 606/172; 33/483, 511, 512

[56] References Cited

U.S. PATENT DOCUMENTS

| | | | |
|---|---|---|---|
| 146,673 | 1/1874 | Hessett | 33/483 |
| 2,799,938 | 7/1957 | Anderson . | |
| 3,230,628 | 1/1966 | Hite . | |
| 4,776,347 | 10/1988 | Matthews | 600/587 |
| 5,018,531 | 5/1991 | Hartman . | |
| 5,092,054 | 3/1992 | Cipiti | 33/510 |
| 5,461,795 | 10/1995 | Kok . | |
| 5,487,223 | 1/1996 | Krane . | |
| 5,605,165 | 2/1997 | Sessions et al. . | |

FOREIGN PATENT DOCUMENTS 1202589   1/1960   France .

*Primary Examiner*—Max Hindenburg
*Attorney, Agent, or Firm*—Kenneth L. Tolar

[57] ABSTRACT

A skin blemish measuring device includes an elongated tubular member having measuring indica on its exterior surface. An indicator ring is slidably mounted on the tubular member. The lower end of the tubular member is inserted into a wound or is placed on the patient's skin immediately adjacent a protruding sore and the indicator ring is slid downwardly until the ring rests on the surface of the patient's skin or on top of the sore. The ring will then be aligned with one of the measurement indica that corresponds to the size of the blemish.

5 Claims, 1 Drawing Sheet

DISPOSABLE WOUND MEASURING DEVICE AND METHOD

BACKGROUND OF THE INVENTION

The present invention relates to a device that allows a healthcare worker to easily ascertain the depth of wounds, sores and similar skin blemishes in order to accurately monitor the healing process.

DESCRIPTION OF THE PRIOR ART

Healthcare workers periodically measure a patient's skin blemishes in order to monitor the healing process. Typically, the healthcare worker uses an elongated wooden swab covered with a fibrous outer layer to measure such wounds. The wooden swabs, however, are susceptible to breakage and often deposit fibrous material in the wound increasing the likelihood of infection. Although various blemish measuring devices exist in the prior art, none include the features and advantages according to the present invention. For example, U.S. Pat. No. 5,605,165 issued to Sessions et al relates to a device and method for measuring a wound including a transparent sheet formed of a pair of separable sections. The second section includes indica thereon which allows a user to determine the surface area of the wound after an outline of the wound is traced thereon.

U.S. Pat. No. 5,461,795 issued to Kok discloses a ruler having two sets of graduation marks thereon, each having a different visual impact.

U.S. Pat. No. 5,487,223 issued to Krane discloses a tape measure having a plurality of alternately disposed slots thereon, each corresponding to graduations on the scale.

U.S. Pat. No. 5,018,531 issued to Hartman discloses a skin blemish measuring and recording system and method. The device includes a color scale corresponding to varying skin blemishes, a blemish size gauge, a distance scale and a body map for recording the location of the blemish.

U.S. Pat. No. 3,230,628 issued to Hite discloses a gauge for measuring orthopedic screws.

U.S. Pat. No. 2,799,938 issued to Anderson discloses an evaluating device.

Although various measuring devices exist in the prior art, none relate to a device having an indicator ring slidably mounted thereon that allows a health care worker to quickly determine the wound depth.

SUMMARY OF THE INVENTION

The present invention relates to a device for measuring a skin blemish. The device comprises an elongated tubular member with a plurality of measurement indicia disposed on the exterior surface thereof. An indicator ring is slidably mounted on the tubular member and has an arrow thereon. To use the device, the lower end of the tubular member is inserted into a recessed wound or placed on the skin alongside a protruding growth such as an ulcer or sore, and the indicator ring is slid downwardly until it abuts the skin surrounding the wound or rests on top of the growth. Accordingly, the measurement mark aligned with the arrow corresponds to the size of the blemish. It is therefore an object of the present invention to provide a blemish measuring device that is easy to use and inexpensive to manufacture.

It is another object of the present invention to provide a blemish measuring device that allows a healthcare worker to quickly measure the depth of a recessed wound.

It is yet another object of the present invention to provide a blemish measuring device that allows a healthcare worker to more accurately measure the depth of a recessed wound.

It is yet another object of the present invention to provide a wound measuring device that also allows a healthcare worker to quickly measure the size of an external growth such as an ulcer or cist. Other objects, features and advantages of the present invention will become readily apparent from the following detailed description of the preferred embodiment when considered with the attached drawings and the appended claims.

DESCRIPTION OF THE PREFERRED EMBODIMENT

Figure 1:
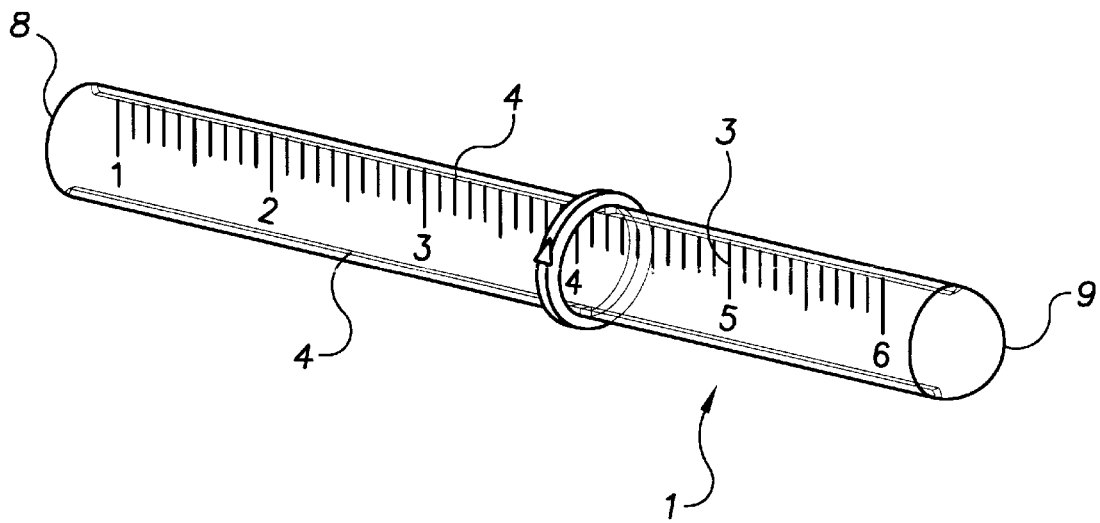
FIG. 1 is a perspective view of the inventive device.
Figure 2:
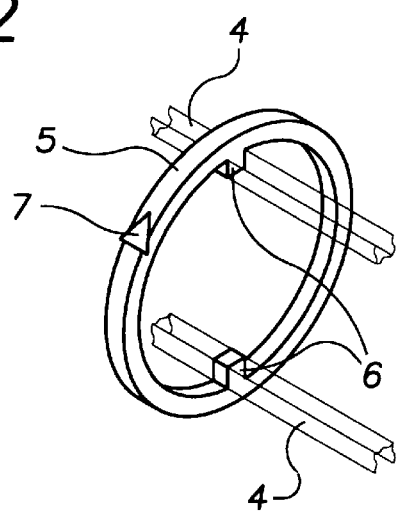
FIG. 2 is a close-up perspective view of the sliding indicator ring.
Figure 3:
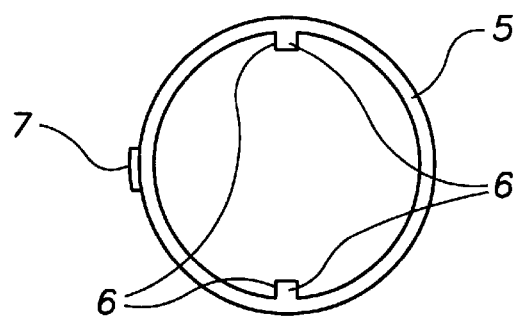
FIG. 3 is a plan view of the sliding indicator ring.

Referring now to FIGS. 1 through 3, the present invention relates to a device for measuring a wound. The device comprises an elongated tubular member 1 having a lower end 8, an upper end 9 and an exterior surface. The upper and lower ends are rounded or tapered to minimize discomfort to the patient. Disposed on the exterior surface are a plurality of measurement indicia 3 arranged in predetermined graduated units such as centimeters, millimeters, fractions of an inch, etc. The measurement indicia incrementally increase from the lower end to the top end.

The exterior surface of the tubular member also includes a pair of opposing longitudinal elongated grooves 4 thereon. An indicator ring 5 having an inner and outer surface encompasses the tubular member. A pair of opposing nodules 6 extend from the inner surface, each of which is slidably received within a groove 4 allowing the ring to slide up and down along the tubular member. The indicator ring also includes an arrow 7 on its outer surface that aligns with one of the indica to visually indicate the size of a wound. Each groove terminates a predetermined distance from each end of the tubular member thereby preventing the ring from sliding off the tubular member.

To use the above described device, the lower end of the tubular member is inserted into a patient's wound or is placed on the patient's skin immediately adjacent an external growth. The indicator ring is slid downwardly towards the patient until it rests on the patient's skin or on top of the growth. The depth of the wound may therefore be readily ascertained by determining which measurement mark is aligned with the arrow on the indicator ring. Preferably, the ring includes a locking mechanism that locks the ring once a measurement is taken. Accordingly if the health care worker forgets to immediately record the measurement, he or she can record it later.

The tubular member and indicator ring are preferably constructed with plastic whereby the device may be discarded after use. However, as will be readily apparent to those skilled in the art, the size, shape, and materials of construction of the various components may be varied without departing from the spirit of the present invention. In addition, the length of the tubular member as well as the units and unit increments may be varied.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

What is claimed is:

1. A wound measuring device comprising:

an elongated member having a lower end, an upper end and an exterior surface;

a plurality of measurement indicia on the exterior surface of said elongated member;

a ring slidably mounted on said tubular member which is moved upwardly and downwardly to measure a blemish; said ring including an inner surface having a pair of nodules thereon, each nodule slidably received within a longitudinal groove on the exterior surface of said elongated member.

2. A wound measuring device according to claim 1 wherein said ring further includes an outer surface having an arrow thereon.

3. A wound measuring device according to claim 1 wherein said elongated member is tubular.

4. A wound measuring device according to claim 1 wherein each of said grooves terminates a predetermined distance from said upper and lower ends thereby retraining said ring on said tubular member.

5. A wound measuring device according to claim 1 wherein said upper and lower ends are rounded to minimize discomfort to a patient.

* * * * *